United States Patent
Ni et al.

(10) Patent No.: US 10,335,408 B2
(45) Date of Patent: Jul. 2, 2019

(54) COMPOSITIONS AND METHODS OF USING NINTEDANIB FOR IMPROVING GLAUCOMA SURGERY SUCCESS

(71) Applicant: Cloudbreak Therapeutics, LLC, Irvine, CA (US)

(72) Inventors: Jinsong Ni, Irvine, CA (US); Rong Yang, Irvine, CA (US)

(73) Assignee: Cloudbreak Therapeutics, LLC, Irvine, CA (US)

( * ) Notice: Subject to any disclaimer, the term of this patent is extended or adjusted under 35 U.S.C. 154(b) by 0 days.

(21) Appl. No.: 16/131,945

(22) Filed: Sep. 14, 2018

(65) Prior Publication Data
US 2019/0015409 A1    Jan. 17, 2019

Related U.S. Application Data

(63) Continuation of application No. PCT/US2017/034792, filed on May 26, 2017.

(60) Provisional application No. 62/344,870, filed on Jun. 2, 2016, provisional application No. 62/344,878, filed on Jun. 2, 2016.

(51) Int. Cl.
| | |
|---|---|
| *A61K 31/496* | (2006.01) |
| *A61P 27/06* | (2006.01) |
| *A61K 9/08* | (2006.01) |
| *A61K 45/06* | (2006.01) |
| *A61K 9/00* | (2006.01) |
| *A61K 9/107* | (2006.01) |

(52) U.S. Cl.
CPC .......... *A61K 31/496* (2013.01); *A61K 9/0048* (2013.01); *A61K 9/0051* (2013.01); *A61K 9/08* (2013.01); *A61K 9/107* (2013.01); *A61K 45/06* (2013.01); *A61P 27/06* (2018.01)

(58) Field of Classification Search
CPC .. A61K 31/496; A61K 9/0048; A61K 9/0051; A61K 9/08; A61K 9/107; A61K 45/06; A61P 27/06
USPC ....................................................... 514/157
See application file for complete search history.

(56) References Cited

U.S. PATENT DOCUMENTS

| | | |
|---|---|---|
| 2015/0258120 A1 | 9/2015 | Zarnitsyn et al. |
| 2015/0265469 A1 | 9/2015 | Olson |

FOREIGN PATENT DOCUMENTS

| | | |
|---|---|---|
| WO | WO 2016/029191 | 2/2016 |

OTHER PUBLICATIONS

Hostettler et al Respiratory research 2014, 15:157 (Year: 2014).*
Amoozgar et al., "A role for antimetabolites in glaucoma tube surgery: current evidence and future directions.", Curr Opin Ophthalmol , 27(2): 164-9, 2016.
International Search Report and Written Opinion in Application No. PCT/US17/34792, dated Oct. 25, 2017, 14 pages.
Schlunck et al., "Conjunctival fibrosis following filtering glaucoma surgery.", Exp Eye Res., 142: 76-82, 2016.
Van Bergen et al., "Inhibition of placental growth factor improves surgical outcome of glaucoma surgery.", J Cell Mol Med., 17(12): 1632-43, 2013.
Vandewalle et al., "Intracameral bevacizumab as an adjunct to trabeculectomy: a 1-year prospective, randomised study.", Br J Ophthalmol , 98(1): 1-6, 2013.
Wong et al., "Matrix metalloproteinase inhibition modulates post-operative scarring after experimental glaucoma filtration surgery.", Invest Ophthalmol Vis Sci., 44(3): 1097-1103, 2003.
AVASTIN® Label, Revised Sep. 2011.
Aversa et al., "Linifanib: current status and future potential in cancer therapy", Expert Rev. Anticancer Ther. Early online, 1-11, 2015.
Bhartiya et al., "The Need to maintain Intraocular Pressure over 24 Hours", Journal of Current Glaucoma Practice, 6(3): 120-123, 2012.
Brandao et al., "Update on Minimally Invasive Glaucoma Surgery (MIGS) and New Implants", Journal of Ophthalmology, 12 pages, 2013.
Chaudhary et al., "XEN Gel Implant: a new surgical approach in glaucoma", Expert Review of Medical Devices, 15:1, 47-59, 2018.
Daniels et al "Imatinib Treatment for Idiopathic Pulmonary Fibrosis Randomized Placedo-controlled Trial Results", J Respir Crit Care Med vol. 181. pp. 604-610, 2010.
Gedde et al., "Treatment Outcomes in the Tube Versus Trabeculectomy (TVT) Study After Five Years of Follow-up", Am J Ophthalmol., 153(5): 789-803, 2012.
Hojjat-Farsangi, "Small-Molecule Inhibitors of the Receptor Tyrosine Kinases: Promising Tools for Targeted Cancer Therapies", Int. J. Mol. Sci., 15, 13768-13801, 2014.
Kaplowitz et al., "Techniques and Outcomes of Minimally-Invasive Trabecular Ablation and Bypass Surgery",Br J Ophthalmol , 98(5): 579-585, 2014.
Katoh, "FGFR inhibitors: Effects on cancer cells, tumor microenvironment and whole-body homeostatis (Review)", International Journal of Molecular Medicine 38; 3-15, 2016.
Kay et al., "Imatinib Mesylate Treatment of Nephrogenic Systemic Fibrosis", Arthritis & Rheumatism, vol. 58, No. 8, pp. 2543-2548, 2008.
Kitagawa et al., "Activity-based kinase profiling of approved tyrosine kinase inhibitors",Genes to Cells, 18, 110-122, 2013.
Lee et al., "Pivotal role of vascular endothelial growth factor pathway in tumor angiogenesis", ASTR, 8 pages, 2015.
Lucentis® Label, Clinical Trial Date Dec. 2011.
OFEV Capsules Approval Letter, Application No. 205832Orig1s000, 8 pages, Approval date Oct. 15, 2014.
Ornitz et al., "The Fibroblast Growth Factor signaling pathway", WIREs Dev Biol., vol. 4, 215-266, 2015.

(Continued)

*Primary Examiner* — Yevgeny Valenrod
(74) *Attorney, Agent, or Firm* — Fish & Richardson P.C.

(57) ABSTRACT

Compositions and methods of using nintedanib for improving the success rate of glaucoma filtration surgery are disclosed herein. Nintedanib can be used alone or in combination with an anti-metabolite drug in a topical or implant eye formulation.

27 Claims, 3 Drawing Sheets

(56) References Cited

OTHER PUBLICATIONS

Pozarowska et al., "The era of anti-vascular endothelial growth factor (VEGF) drugs in ophthalmology, VEGF and anti-VEGF therapy", Cent. Eur. J. Immunol., 41 (3): 311-316, 2016.

* cited by examiner

COMPOSITIONS AND METHODS OF USING NINTEDANIB FOR IMPROVING GLAUCOMA SURGERY SUCCESS

CLAIM OF PRIORITY

This application is a continuation of International Application Number PCT/US2017/034792, filed May 26, 2017, which claims the benefit of U.S. Provisional Patent Application Ser. No. 62/344,878, filed on Jun. 2, 2016, and U.S. Provisional Patent Application Ser. No. 62/344,870, filed on Jun. 2, 2016, the entire contents of each are hereby incorporated by reference.

TECHNICAL FIELD

The present disclosure relates to ocular compositions comprising nintedanib and methods of use thereof for improving the success rate of glaucoma surgery.

BACKGROUND

Glaucoma refers to a group of eye conditions that damage the optic nerve, which is often caused by an abnormally high pressure in the eye. One way to reduce pressure in an eye with glaucoma is to surgically create a drain in the eye. This type of surgery is called a glaucoma filtration surgery, e.g., trabeculectomy. In glaucoma surgery, a piece of tissue in the drainage angle of the eye is removed, creating an opening. This new opening creates a drain, allowing fluid to drain out of the eye. The eye pressure is reduced because fluid can now drain with relative ease through the new opening into a reservoir (bleb) underneath the conjunctiva. The fluid is then absorbed by the body.

As a result of glaucoma filtration surgery, scarring and fibrosis can develop at the surgical site. The scarring and fibrosis often results in a gradual reduction of filtration and loss of control of intraocular pressure. Excess fibrosis is a key factor leading to scar formation and the failure of glaucoma filtration surgery. Current treatments for reducing the failure are still inadequate and need improvements.

SUMMARY

In certain aspects, the disclosure provides a method for improving the success rate of glaucoma surgery (e.g., glaucoma filtration surgery) by administering nintedanib to the eye of a subject in need of such treatment. One aspect features a method for adjunctive treatment associated with glaucoma filtration surgery in a subject comprising administering to a subject in need thereof an effective amount of a composition comprising nintedanib or a pharmaceutically acceptable salt thereof. The method improves the success rate of glaucoma surgery. Glaucoma surgery includes, for example, the classic trabeculectomy method, or a minimally invasive glaucoma surgery (MIGS) method selected from the group consisting of Trabectome, gonioscopy-assisted transluminal trabeculectomy, excimer laser trabeculostomy, and endoscopic cyclophotocoagulation. The glaucoma surgery performed may also be a MIGS procedure for implantation of an ocular filtration device, wherein the ocular filtration device is an ocular stent. For example, the ocular filtration device may be selected from the group consisting of a XEN® gel stent (e.g. subconjunctival stent), an iStent® or, Hydrus™ microstent (Schlemm's canal stents), and CyPass® microstent (e.g. suprachoroidal stent).

In some aspects of the methods disclosed herein, the amount of nintedanib administered to the subject is effective to extend the duration of lower IOP, increase either the absolute success rate or the qualified success rate for at least 10 days, at least 90 days, at least 365 days, at least 750 days, or at least 3650 days following surgery; or wherein the amount of nintedanib administered is effective to prolong bleb survival.

In some aspects, the nintedanib composition is administered in the form of topical ocular formulation (e.g., a topical eye drop) or implant. In some examples, the nintedanib is in a topical ocular formulation administered topically to the affected eye. In certain aspect, the concentration of nintedanib in the formulation is from 0.001% to 10% by weight or by volume the total amount of composition. In certain aspects, the topical ocular formulation is a solution, a suspension or an emulsion. In another aspect, nintedanib is in an implant or semi-solid sustained release formulation injected into the affected eye. In certain aspects, the amount of nintedanib in the implant is from 1 µg to 100 mg.

In certain aspects, the disclosed methods are performed by the combination of nintedanib and an antimetabolite drug. The antimetabolite drug can be, but not limited to, Mitomycin C, 5-Fluorouracil, Floxuridine, Cytarabine, 6-Azauracil, Azathioprine, Methotrexate, Mycophenolate Mofetil, and Thiotepa.

In another aspect, the disclosed methods reduce scar formation in glaucoma surgery by attenuating abnormal vascularity and fibrosis at the surgical site. In certain aspects, the disclosed methods are performed before operation, in conjunction with operation or after operation, to reduce failure in glaucoma surgery. Thus, in some aspects, the amount of nintedanib administered is effective to reduce scar formation at the site of the surgery. In some aspects, the amount nintedanib administered is effective to extend the duration of lower IOP for at least 10 days, at least 365 days, or at least 3650 days following surgery. In some aspects, the amount of nintedanib administered is effective to prolong bleb survival As used herein, the term "one or more" includes at least one, more suitably, one, two, three, four, five, ten, twenty, fifty, one-hundred, five-hundred, etc., of the item to which "one or more" refers.

The term "subject" refers to an animal or human, or to one or more cells derived from an animal or human. Preferably, the subject is a human. Subjects can also include non-human primates. A human subject can be known as a patient.

Unless otherwise defined, all technical and scientific terms used herein have the same meaning as commonly understood by one of ordinary skill in the art to which this invention belongs. Methods and materials are described herein for use in the present invention; other suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
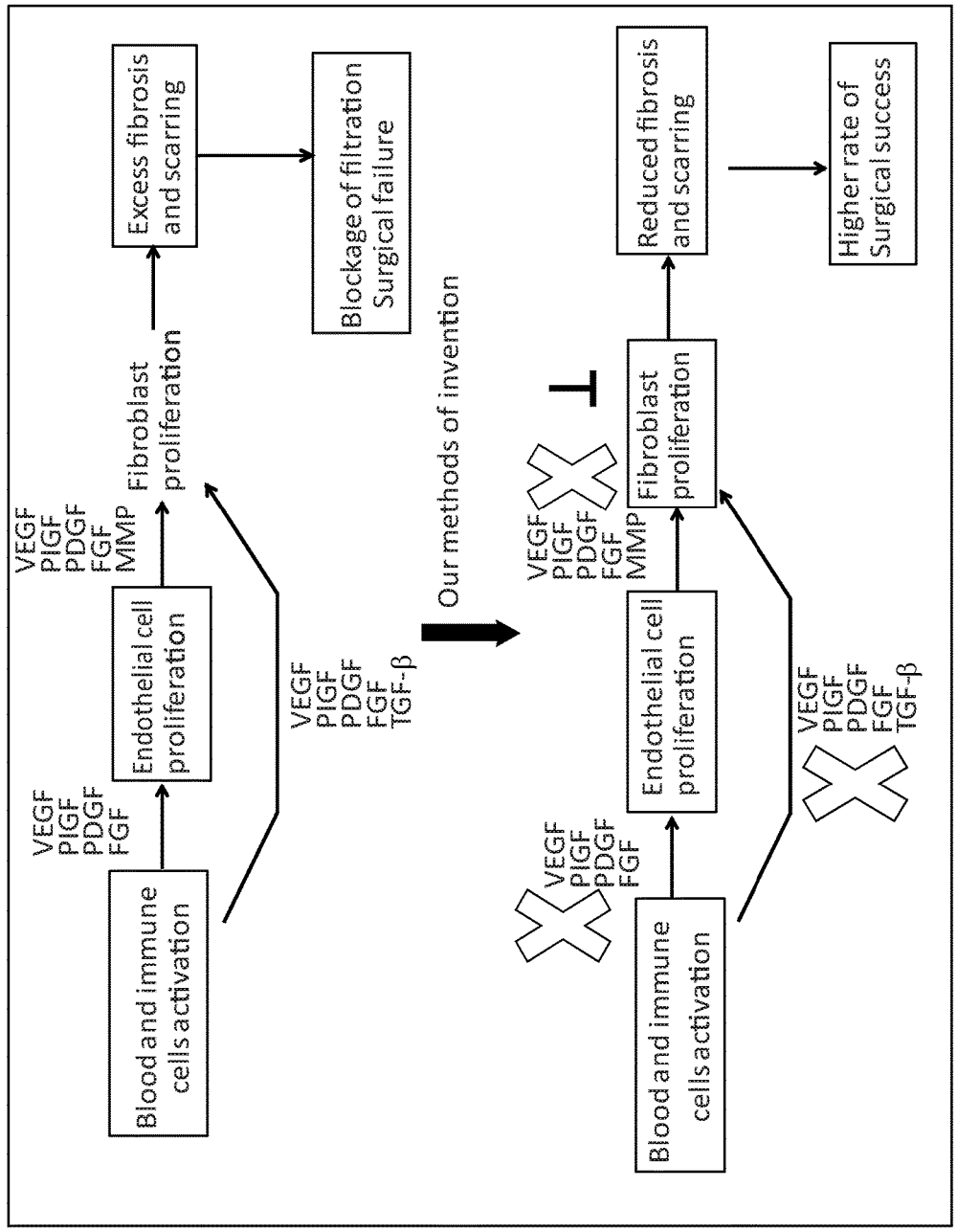
FIG. 1 is a flow chart demonstrating an exemplary mechanism to reduce excess scar formation and to improve the success rate of glaucoma surgery.

Glaucoma is a group of diseases that are characterized by the death of retinal ganglion cells ("RGCs"), specific visual field loss, and optic nerve atrophy. Glaucoma is a leading cause of blindness in the world. A variety of treatment options, effective to reduce intraocular pressure ("IOP"), are available to control, and perhaps to slow, the progression of the disease. Treatment options include, for example, pharmaceutical therapy (i.e., IOP-lowering drugs), laser eye surgery, and/or conventional surgical methods, such as glaucoma filtration surgery (or also known as filtering surgery or trabeculectomy).

Despite the wide usage of topical IOP-lowering drugs in the developed countries, glaucoma surgery is still commonly practiced in other parts of the world, especially for closed-angle glaucoma. Glaucoma surgery has the advantage of low cost over time and doesn't have to deal with compliance issues associated with topical eye drops that need multiple applications per day. The traditional glaucoma filtration surgery and trabeculectomy have high failure rates (Schlunck et al. Exp Eye Res. 2016; 142:76-82) and methods of implanting an ocular filtration device, e.g., a glaucoma drainage device, also have long term failure problems (Amoozgar et al. Curr Opin Ophthalmol. 2016; 27(2):164-9). The failures are due to excessive postoperative wound healing with subsequent fibrosis and scar formation that obstruct drainage. The damage to tissue by surgery often induces pro-inflammation and pro-fibrogenic factors that lead to abnormal extracellular matrix change and fibrosis. Myofibroblast hyper-proliferation induced by these factors subsequently causes excessive fibrosis and scar formation.

The antimetabolite drug, mitomycin C (MMC) has been administered during or after glaucoma surgery as an anti-scaring agent. Another antimetabolite drug, 5-fluorouracil (5-FU), is also used mainly by local injection during follow-up (Schlunck et al. Exp Eye Res. 2016; 142:76-82). These antimetabolite drugs work by blocking fast proliferating fibroblasts. Their activities are not selective and are known to cause side effects. For example, the anti-cell division activity sometimes causes bleb leakage post-surgery. Better postoperative management of glaucoma surgery is still an unmet medical need.

Due to the multi-factorial causes of scar formation following glaucoma surgery, targeting any single pathway alone may not be sufficient to improve surgery success. The present disclosure improves glaucoma surgery success by administering to the eye a composition with the following key attributes: 1) the composition will inhibit several important pathological pathways simultaneously and these pathways are disclosed below; 2) the composition utilizes small molecule drug(s) as opposed to antibody drugs to achieve a more efficient drug delivery to the target tissue; 3) the composition is a topical formulation in the form of either an eye drop or implant for convenient and consistent drug delivery to the site of surgery; and 4) the composition contains nintedanib, which can be used in combination with an antimetabolite drug to achieve an additive or synergistic effect in improving the success of glaucoma filtration surgery.

The disclosure provides a method of using a topical formulation (e.g., topical eye drop, implant) comprising nintedanib, before, during or after surgery. Nintedanib meets the requirement of inhibiting vascular endothelial growth factor ("VEGF") receptors ("VEGFR") 1-3, platelet-derived growth factor receptor ("PDGFR")-α and -β and fibroblast growth factor receptor 2 ("FGFR2") to achieve the needed efficacy.

Without being bound to theory, it is understood that it is important to inhibit all VEGFR members because of the need to block placental growth factor ("PlGF") in addition to VEGF. PlGF only acts on pathologic angiogenesis and inflammation and contributes more to the problems associated with glaucoma surgery (Van Bergen et al. J Cell Mol Med. 2013; 17(12):1632-43). For glaucoma filtration surgery, the disclosed methods also inhibit FGFR2 due to its function in scar formation. The topical formulation disclosed herein allows for convenient treatment before, during and after surgery. The mechanism for improving glaucoma surgery success rate provided by the present disclosure is summarized in FIG. 1, which shows that nintedanib, in a suitable ocular formulation, would simultaneously block signal pathways of the key pathogenic factors involved in excess wound healing, including PlGF, VEGF, PDGF, FGF, and would enhance the success of glaucoma surgery by reducing scar formation.

As used herein, the term "improving glaucoma surgery success" means extending the duration of reduced (i.e., lower) IOP for a period of at least 10 days, at least 90 days, at least 365 days, at least 750 days, or at least 3650 days following surgery, an increase of IOP-reduction percentage comparing the pre-surgical baseline over a given period of time (e.g., at least 10 days, at least 90 days, at least 365 days, at least 750 days, or at least 3650 days) after surgery, increase of the absolute (also known as complete) success rate (defined as percent of patients kept within normal IOP range with reduced IOP in relation to the baseline without any glaucoma medication) over a given period of time, increase of qualified success rate (defined as percent of patients kept within normal IOP range with reduced IOP in relation to the baseline with the help of glaucoma medications) over a certain period of time (e.g., at least 10 days, at least 90 days, at least 365 days, at least 750 days, or at least 3650 days), improvement of the bleb grade and survival over a certain period of time (e.g., at least 10 days, at least 90 days, at least 365 days, at least 750 days, or at least 3650 days).

As used herein, "normal IOP" or "normal IOP range" refers to intraocular pressure in the human eye of between about 5 mm Hg to about 22 mm Hg, or about 10 mm Hg to about 21 mm Hg.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development;

or (c) relieving the disease symptom(s), i.e., causing regression of the disease and/or symptom(s). Those in need of treatment include those already inflicted (e.g., those with high IOP, those with an infection, etc.) as well as those in which prevention is desired (e.g., those with increased susceptibility to glaucoma, those suspected of having high IOP, etc.).

Nintedanib {Methyl (3Z)-3-{[(4-{methyl[(4-methylpiperazin-1-yl) acetyl] amino}phenyl)amino] (phenyl)methylidene}-2-oxo-2,3-dihydro-1H-indole-6-carboxylate} is a kinase inhibitor as described herein. Nintedanib inhibits primarily receptor tyrosine kinases including, for example vascular endothelial growth factor receptor (VEGFR 1-3), platelet-derived growth factor receptor (PDGFR α and β), fibroblast growth factor receptor (FGFR 1-4).

Formulations and Dosing Regimen

The methods described herein include the manufacture and use of pharmaceutical compositions, which include compounds identified by a method described herein as active ingredients. Also included are the pharmaceutical compositions themselves.

Pharmaceutical compositions typically include pharmaceutically acceptable excipients. As used herein the language "pharmaceutically acceptable excipient" or "pharmaceutically acceptable carrier" includes saline, solvents, dispersion media, coatings, antibacterial and antifungal agents, isotonic and absorption delaying agents, and the like, compatible with pharmaceutical administration.

The phrase "pharmaceutically acceptable salt" as used herein means those salts of a compound of interest that are safe and effective for administration to a mammal and that possess the desired biological activity. Pharmaceutically acceptable acid salts include, but are not limited to hydrochloride, hydrobromide, hydroiodide, nitrate, sulfate, bisulfate, phosphate, acid phosphate, isonicotinate, carbonate, bicarbonate, acetate, lactate, salicylate, citrate, tartrate, propionate, butyrate, pyruvate, oxalate, malonate, pantothenate, bitartarte, ascorbate, succinate, maleate, gentisinate, fumarate, gluconate, glucaronate, saccharate, formate, benzoate, glutamate, methanesulfonate, thanesulfonate, benzenesulfonate, p-toluenesulfonate and pamoate (i.e., I,I' methylene-bis-(2-hydroxy-3-naphthoate)) salts. Suitable base salts include, but are not limited to, aluminum, calcium, lithium, magnesium, potassium, sodium, zinc, bismuth, and diethanolamine salts.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions, suspensions, creams, ointments, gels, gel-forming liquid, suspension containing liposomes or micelles, spray or formulation, or emulsions used for ophthalmic application can include the following components: a sterile diluent such as water for injection, saline solution, fixed oils, polyethylene glycols, glycerin, propylene glycol or other synthetic solvents; antibacterial agents; antioxidants; chelating agents; buffers such as acetates, citrates or phosphates and agents for the adjustment of tonicity such as sodium chloride or dextrose. The pH can be adjusted with acids or bases, such as hydrochloric acid or sodium hydroxide.

Pharmaceutical compositions suitable for injectable use can include sterile aqueous solutions (where water soluble) or dispersions and sterile powders for the extemporaneous preparation of sterile injectable solutions or dispersion. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially.

The pharmaceutical compositions can be included in a container, pack, or dispenser together with instructions for administration.

Compositions and formulations of nintedanib, can be administered topically (e.g., as a topical ocular formulation) or as an injection of semi-solid formulation or solid implant, or by any other suitable methods known in the art. While it is possible to use the agent disclosed herein for therapy as is, it may be preferable to administer the agent as a pharmaceutical formulation, e.g., in admixture with a suitable pharmaceutical excipient, diluent, or carrier selected with regard to the intended route of administration and standard pharmaceutical practice. Pharmaceutical formulations include at least one active compound, in association with a pharmaceutically acceptable excipient, diluent, and/or carrier.

The pharmaceutical composition disclosed herein may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition are outweighed by the therapeutically beneficial effects.

Effective doses of the compositions of the present disclosure, for the treatment of conditions vary depending upon many different factors, including means of administration, target site, physiological state of the subject, whether the subject is human or an animal, other medications administered, and whether treatment is prophylactic or therapeutic. Treatment dosages can be titrated using routine methods known to those of skill in the art to optimize safety and efficacy.

In some instances, the topical ocular formulation is a solution, a suspension, creams, ointments, gels, gel-forming liquid, suspension containing liposomes or micelles, spray formulation, or an emulsion. In some cases, the topical ocular formulation also includes one or more pharmaceutically acceptable excipients selected from stabilizers, surfactants, polymer base carriers, gelling agents, organic co-solvents, pH active components, osmotic active components and with or without preservatives. In some cases, the sustained release semi-solid formulation, sustained release solid formulation or ocular implant is injected into the affected eye. In some embodiments, the sustained release semi-solid formulation, sustained release solid formulation or ocular implant further comprises a pharmaceutically acceptable excipient. In some cases, the sustained release semi-solid formulation, sustained release solid formulation or ocular implant includes a multikinase inhibitor, the antimetabolite, or combination thereof; and a biodegradable polymer selected from polylactic acid (PLA), polyglycolic acid (PLGA) and polylactic acid and polyglycolic acid copolymers.

Administration of a composition or formulation can be once a day, twice a day, three times a day, four times a day or more often. Frequency may be decreased during a treatment maintenance phase of the treatment, e.g., once every second or third day instead of every day or twice a day. The dose and the administration frequency can be adjusted based on the judgment of the treating physician, for example, taking into account the clinical signs, pathological signs and clinical and subclinical symptoms of a disease of the conditions treated with the present methods, as well as the patient's clinical history.

It will be appreciated that the amount of an agent disclosed herein required for use in treatment will vary with the route of administration, the nature of the condition for which treatment is required, and the age, body weight and condition of the patient, and will be ultimately at the discretion of the attendant physician. Compositions will typically contain an effective amount of nintedanib. Preliminary doses can be determined according to animal tests, and the scaling of dosages for human administration can be performed according to art-accepted practices.

Length of treatment, i.e., number of days, will be readily determined by a physician treating the subject; however, the number of days of treatment may range from about 1 day to about 365 days. As provided by the present methods, the efficacy of treatment can be monitored during the course of treatment to determine whether the treatment has been successful, or whether additional (or modified) treatment is necessary.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). Dosage forms for nintedanib can be readily determined by the ordinarily skilled artisan, and can e.g., be obtained in animal models and in clinical studies reported in the literatures, for determining dosage, safety and efficacy according to standard methods known in the art. The exact formulation, route of administration and dosage can be chosen by the individual physician in view of the patient's condition.

Compositions for use in the present methods may include nintedanib at a concentration of 0.001% to 10% by weight or by volume the total amount of composition. For example, an aqueous composition comprises 0.001%, 0.01%, 0.1%, 0.5%, 1.0%, 1.5%, 2.0%, 5.0% or up to 10% nintedanib.

As will be familiar to those skilled in the art, administration to the eye of an aqueous solution may be in the form of a "drop" or number of drops (e.g. of nintedanib solution) from a dropper or pipette or other dedicated sterile devices. Such drops will typically be up to 50 microliters in volume, but may be smaller e.g. less than 10 microliters.

EXAMPLES

The invention is further described in the following examples, which do not limit the scope of the invention described in the claims.

Example 1: Rabbit Glaucoma Surgery Model

The rabbit glaucoma surgery model is used to illustrate use of the presently disclosed methods for improving the success of glaucoma filtration surgery. Specifically, an established rabbit model of glaucoma filtration surgery would be used to study the effects of nintedanib 0.2% solution on the wound-healing events after surgery. The surgical procedure is as described in Wong et al. (Wong et al. Invest Ophthalmol Vis Sci. 2003; 44(3):1097-1103). Briefly, a partial thickness 8-0 silk corneal traction suture is placed superiorly, and the eye pulled down. A fornix based conjunctival flap is raised, after which a blunt dissection of the subconjunctival space is performed of approximately 5 mm along the limbus and 8 mm posteriorly. A microvitreoretinal (MVR) blade is used to make a partial-thickness scleral incision 3 to 4 mm behind the limbus, and a scleral tunnel to the corneal stroma is fashioned. A 22-gauge, 25-mm intravenous cannula (Venflon 2; Beckton Dickinson, Oxford, UK) is passed through a scleral tunnel anteriorly until the cannula needle is visible in the clear cornea. Entry into the anterior chamber is made with a cannular needle, which is then withdrawn as the cannula is advanced to the mid-pupillary area. The cannula is trimmed and beveled at its scleral end so that it protrudes 1 mm from the insertion point, and a 10-0 nylon suture is placed to fix the tube to the scleral surface. The conjunctival incision is closed with two interrupted sutures and a central, mattress-type 10-0 nylon suture attached to a needle (B/V 100-4; Ethicon) to give a water-tight closure. One drop each of guttae chloramphenicol and Betnesol-N (Glaxo Wellcome, Uxbridge, UK) ointment is instilled at the end of surgery.

Twenty female New Zealand White rabbits (2-2.4 kg, 12-14 weeks old; Charles River) would be acclimatized for 5 days before the experiments start. Glaucoma surgery would be performed on the left eye as described. After surgery, the rabbits would be arranged into two groups and one group would be treated with vehicle and another with nintedanib 0.2% solution. Treatments would begin immediately after surgery and the treatment would be TID for 2 weeks. The survival of the bleb formed by the surgery and the intraocular pressure (IOP) would be followed for 28 days. Histological analysis of the scar tissue would be performed at the end of the study.

Results

Figure 2:
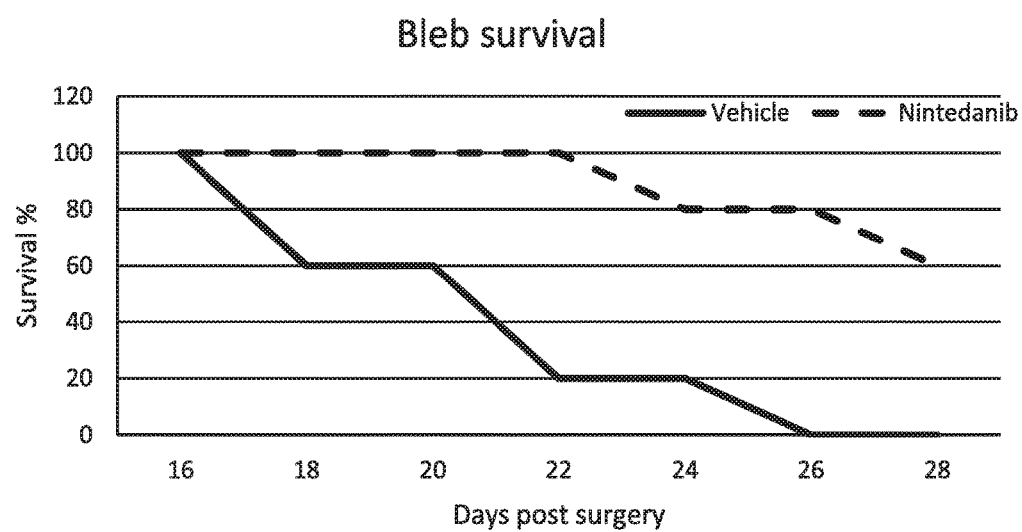
FIG. 2 is a graph showing bleb survival following glaucoma filtration surgery in a rabbit model.
Figure 3:
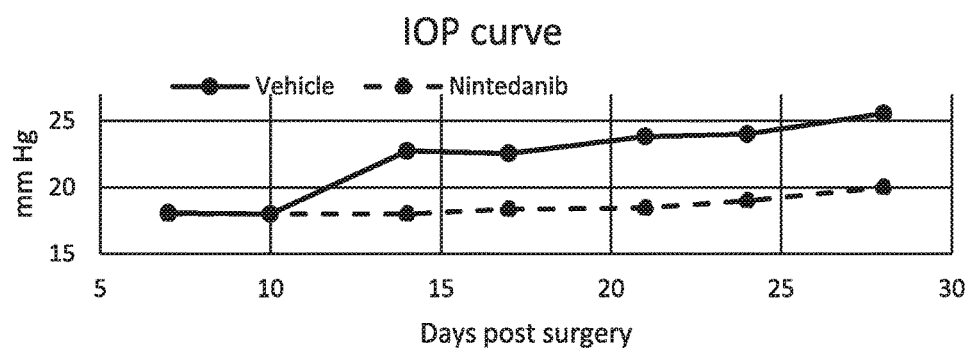
FIG. 3 is a graph showing intraocular pressure (IOP) following glaucoma filtration surgery in a rabbit model.

Surgery success outcome would be significantly prolonged in the nintedanib group compared with the vehicle group. FIG. 2 provides a graph showing the survival curve of the bleb after surgery. As shown in FIG. 2, the nintedanib group would show a substantially prolonged bleb survival comparing to the vehicle group. By the end of study on day 28, no bleb would survive in the vehicle group while most of the bleb would survive in the nintedanib group. FIG. 3 is a graph showing the IOP curve during the follow up period after the surgery. IOP remained low (i.e., below 20 mm in the nintedanib group and increased gradually in the vehicle group. The difference would be statistically significant. In addition to bleb survival and IOP change, histological analysis of scar tissue at the surgical site would show less scar tissue in the nintedanib group than the vehicle group.

The results from this experiment would indicate that the nintedanib 0.2% solution increases the success of glaucoma surgery (i.e., prolonged bleb survival, extended duration of lower IOP following surgery and/or reduced fibrosis/scarring).

Example 2: Topical Ocular Formulations of Nintedanib as Adjunct Therapy to Glaucoma Filtration Surgery Topical nintedanib 0.2% as adjunct therapy to increase success of trabeculectomy in a clinical study. A randomized, double-masked, placebo-controlled, 12-month experimental trial to test the effects of topical nintedanib 0.2% on the success rate of trabeculectomy. The study design would be as described by Vandewalle et. al. (Vandewalle et. al. Br J Ophthalmol. 2014, January; 98(1):73-8).

Patients with medically uncontrolled open-angle glaucoma scheduled for a primary trabeculectomy would be enrolled and randomized to receive one drop TID of either nintedanib or placebo solutions. The treatment would start immediately after surgery and would last for a month. Approximately 150 patients would be enrolled in the study.

Surgeries would be performed under general or retrobulbar anaesthesia by experienced surgeons using a modified Moorfields technique. IOP would be measured by Goldmann applanation tonometry. Two measurements would be taken by masked observers and averaged to determine the mean IOP if two values were within 2 mm Hg. A third measurement would be taken if the difference between the first two determinations is >2 mm Hg.

Patients would be examined on day 1; at weeks 1, 2, and 4; and at months 3, 6, and 12 after trabeculectomy. All patients would go through a comprehensive ophthalmic examination that included measurements of best-corrected visual acuity, slit-lamp examination, including, a Seidel test, IOP measurement, and fundus biomicroscopy with a 90-diopter lens. The number of postoperative IOP-lowering medications, intra- and postoperative complications, and surgical interventions would also be recorded.

Absolute success would be the primary endpoint and would be defined as intraocular pressure (IOP)≤21 mm Hg and >5 mm Hg with at least 20% reduction from baseline and no loss of light perception.

Results

Figure 4:
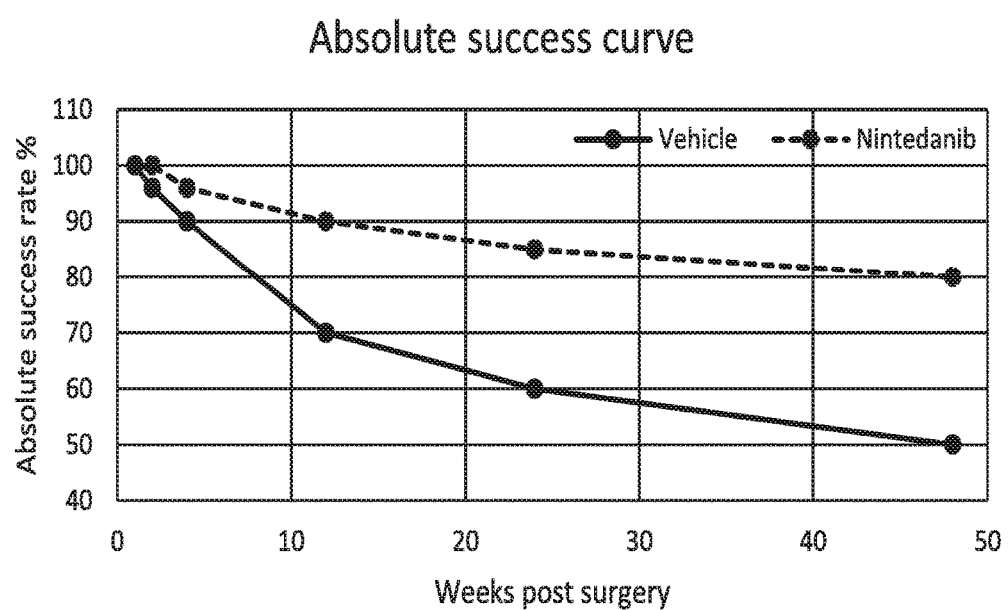
FIG. 4 is a graph showing absolute success of glaucoma filtration surgery in a clinical study according to the methods disclosed herein.

IOP would be effectively reduced in both nintedanib and placebo groups at the 12-month visit when compared to baseline. The absolute success rate of glaucoma surgery, i.e., maintaining IOP of less than about 20 mm Hg for more than 12 months after surgery, would be higher in the nintedanib group vs the placebo group as shown in FIG. 4. At time points after 6 months, the differences would be statistically significant.

Example 3: Formulations

Nintedanib Ophthalmic Solution

The drug product is an isotonic ophthalmic solution prepared in 2-hydroxypropyl beta cyclodextrin or other similar cyclodextrins, and buffer solution, pH range from 5.5 to 8.0. Other viscosity, lubricant, preservative agents might be added to enhance functionality of the formulation. The compositions of the ophthalmic solution are disclosed in Table 1.

TABLE 1

Nintedanib Ophthalmic Solution

| Ingredients | Functions | Concentration Range (% w/v) |
| --- | --- | --- |
| CBT-001 (Nintedanib free base) | Active Pharmaceutical Ingredient | 0.001-10 |
| Sodium carboxymethylcellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate dibasic heptahydrate | Buffer Agent | 0-0.8 |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Suspension

The drug product is an isotonic ophthalmic suspension prepared in carboxymethylcellulose sodium and buffer solution, pH range from 5.5 to 8.0. The drug particle sizes are reduced to below 40 micron. Other viscosity, lubricant, solubilizer, and preservative agents might be added to enhance functionality of the formulation suspension. The compositions are disclosed in Table 2.

TABLE 2

Nintedanib Ophthalmic Suspension

| Ingredients | Functions | Concentration Range (% w/v) |
|---|---|---|
| CBT-001 (Nintedanib free base) | Active Pharmaceutical Ingredient | 0.001-10 |
| Sodium carboxymethylcellulose | Viscosity Agent/dry eye relief | 0-1 |
| Pemulen TR | Viscosity Agent | 0-0.2 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| 2-hydroxypropyl beta cyclodextrin | Solubilizer | 0-10 |
| Sulfobutyl-beta-cyclodextrin | Solubilizer | 0-10 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Poloxamer 188, or 237, or 407 | Solubilizer/lubricant | 0-5 |
| Polysorbate 80 | Solubilizer/lubricant/surfactant | 0-1 |
| Edetate disodium | Chelating Agent/Preservative | 0-0.01 |
| Benzalkonium chloride | Preservative | 0-0.02 |
| Sodium phosphate monobasic monohydrate | Buffer Agent | 0-0.43 |
| Sodium phosphate dibasic heptahydrate | Buffer Agent | 0-0.8 |
| Boric acid | Buffer Agent | 0-0.6 |
| Sodium borate, decahydrate | Buffer Agent | 0-0.045 |
| Citric acid, monohydrate | Buffer Agent/preservative | 0-0.13 |
| Sodium citrate, dihydrate | Buffer Agent/preservative | 0-0.45 |
| Glycerin | Tonicity Agent | 0-2.2 |
| Sodium chloride | Tonicity Agent | 0-0.83 |
| 1N Sodium hydroxide 1N Hydrochloric acid | pH Adjustment | pH 5.5-8.0 |
| Water for injection | Vehicle | Q.S. to 100 |

Nintedanib Ophthalmic Emulsion

The drug product is an isotonic ophthalmic emulsion. The drug is dissolved in the mixture oil phase and emulsifier excipients which is then emulsified and mixed with an aqueous phase with pH range from 5.5 to 8.0. Other viscosity, lubricant, solubilizer, and preservative agents might be added to enhance functionality of the emulsion formulation. The compositions are disclosed in Table 3.

TABLE 3

Nintedanib Ophthalmic Emulsion

| Ingredients | Functions | Concentration (% w/w) |
|---|---|---|
| CBT-001 (Nintedanib free base) | Active Pharmaceutical Ingredient | 0.001-10 |
| Castor oil | Oil solvent | 0-1.25 |
| Polyoxyl-40-Stearate | Emulsifier | 0-0.25 |

TABLE 3-continued

Nintedanib Ophthalmic Emulsion

| Ingredients | Functions | Concentration (% w/w) |
|---|---|---|
| Polysorbate 80 | Solubilizer/Emulsifier/Surfactant | 0-1 |
| Sulfobutyl-β-cyclodextrin | Solubilizer | 0-5 |
| 2-Hydroxypropyl-beta-cyclodextrin | Solubilizer | 0-5 |
| Randomly methylated beta-cyclodextrin | Solubilizer | 0-5 |
| α-cyclodextrin | Solubilizer | 0-4 |
| β-cyclodextrin | Solubilizer | 0-1 |
| γ-cyclodextrin | Solubilizer | 0-1 |
| Glycerin | Tonicity Agent | 0-2.2 |
| Sodium Chloride | Tonicity Agent | 0-0.83 |
| Pemulen TR2 | Viscosity Agent | 0-0.1 |
| Sodium carboxymethylcellulose | Viscosity Agent | 0-0.5 |
| Polyvinyl alcohol | Viscosity/Lubrication Agent | 0-1.5 |
| Hypromellose | Lubricant/dry eye relief | 0-1 |
| Carbomers | Lubricant/dry eye relief | 0-0.5 |
| Carmellose sodium | Lubricant/dry eye relief | 0-1 |
| Sodium hyaluronate | Lubricant/dry eye relief | 0-1.5 |
| Polyethylene glycol 400 | Lubricant/dry eye relief | 0-0.4 |
| Propylene glycol | Lubricant/dry eye relief | 0-0.6 |
| Poloxamer 188, or 237, or 407 | Solubilizer/lubricant | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Semi-Solid Formulation

The drug product is an isotonic sustained release semi-solid formulation. The drug is dissolved and/or suspended in a semi-solid medium with pH range from 5.5 to 8.0. Other viscosity, lubricant, solubilizer, and preservative agents might be added to enhance functionality of the sustained release semi-solid formulation. The compositions are disclosed in Table 4.

TABLE 4

Sustained Release Semi-Solid Formulation

| Ingredients | Functions | Concentration (% w/w) |
|---|---|---|
| CBT-001 (Nintedanib free base) | Active Pharmaceutical Ingredient | 0.001-10 |
| Xanthan Gum | Viscosity/Thickener | 0-10 |
| Hydroxypropyl methylcellulose | Viscosity/Thickener | 0-10 |
| Sodium hyaluronate | Viscosity/Thickener | 0-5 |
| Hyaluronic acid | Viscosity/Thickener | 0-5 |
| Boric acid | Buffer | 0-0.6 |
| Sodium borate, decahydrate | Buffer | 0-0.045 |
| Citric acid, monohydrate | Buffer/preservative | 0-0.13 |
| Sodium citrate, dihydrate | Buffer/preservative | 0-0.45 |
| Sodium phosphate, monobasic monohydrate | Buffer | 0-0.43 |
| Sodium phosphate dibasic heptahydrate | Buffer | 0-0.8 |

TABLE 4-continued

Sustained Release Semi-Solid Formulation

| Ingredients | Functions | Concentration (% w/w) |
|---|---|---|
| 1N & 5N Sodium hydroxide 1N Hydrochloric acid | pH Adjustment | pH 5.5-8.0 |
| Water for injection | Aqueous Vehicle | Q.S. 100 |

Nintedanib Sustained Release Implants

The drug product is a solid implant. The drug is mixed and blended with one or more polymers. The mixture of drug and polymers is melted at a predetermined temperature and extruded into a filament with a predetermined diameter size. The formulation filament is cut into a predetermined size of segment which can be implanted into ocular tissues. The compositions are disclosed in Table 5.

TABLE 5

Sustained Release Implants

| Ingredients | Functions | Concentration (% w/w) |
|---|---|---|
| CBT-001 (Nintedanib free base) | Active Pharmaceutical Ingredient | 0.001-10 |
| Poly (D,L-Lactide), i.v. 0.25-0.35 dL/g | Polymer | 0-100 |
| Poly (D,L-Lactide-coglycolide) i.v. 0.14-0.22 dL/g | Polymer | 0-100 |
| Poly (D,L-Lactide), i.v. 0.16-0.25 dL/g | Polymer | 0-100 |
| Polyethylene Glycol 3350 | Polymer | 0-20 |
| Resomer ®RG755S | Polymer | 0-100 |
| Resomer ®RG753H | Polymer | 0-100 |

Without limitation, an example composition, for use in the methods according to the invention, may be modified from existing ophthalmically acceptable compositions.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for improving success rate of glaucoma surgery, comprising administering to an eye of a subject in need thereof a therapeutically effective amount of nintedanib or a pharmaceutically acceptable salt thereof.

2. The method of claim 1, wherein the nintedanib is administered in the form of topical eye drop or implant.

3. The method of claim 1, wherein the amount of nintedanib administered is effective to reduce scar formation or reduce fibrosis at a site of the surgery in the eye of the subject.

4. The method of claim 1, wherein the amount of nintedanib administered is effective to extend the duration of lower intraocular pressure (IOP), increase either the absolute success rate or the qualified success rate for at least 10 days following glaucoma surgery; or wherein the amount of nintedanib administered is effective to prolong bleb survival.

5. The method of claim 1, wherein the nintedanib is administered in a form selected from the group consisting of a semi-solid or solid sustained-release implant injected into the eye of the subject.

6. The method of claim 1, wherein the nintedanib is administered as a topical ocular formulation selected from the group consisting of a solution, suspension, or emulsion.

7. The method of claim 1, wherein the administration is performed before, during or after glaucoma surgery.

8. The method of claim 1, wherein the glaucoma surgery is performed using classic trabeculectomy or a method selected from the group consisting of Trabectome, gonioscopy-assisted transluminal trabeculotomy, excimer laser trabeculostomy, and endoscopic cyclophotocoagulation.

9. The method of claim 1, wherein the glaucoma surgery performed is, for implanting an ocular filtration device.

10. The method of claim 9, wherein the ocular filtration device is an ocular stent.

11. The method of claim 1, wherein nintedanib is administered in combination with a cell-proliferation-inhibiting antimetabolite drug.

12. The method of claim 11, wherein the antimetabolite drug is selected from the group consisting of mitomycin C, 5-fluorouracil, floxuridine, cytarabine, 6-azauracil, azathioprine, methotrexate, mycophenolate mofetil, and thiotepa.

13. A method of adjunctive treatment associated with glaucoma surgery in a subject, the method comprising administering to a subject in need thereof an effective amount of a composition comprising nintedanib or a pharmaceutically acceptable salt thereof.

14. The method of claim 13, wherein the composition is administered in the form of topical eye drop or implant.

15. The method of claim 13, wherein the composition contains an amount of nintedanib effective to reduce scar formation or reduce fibrosis at a site of the surgery in the eye of the subject.

16. The method of claim 13, wherein the composition contains an amount of nintedanib effective to extend the duration of lower IOP, or increase either the absolute or the qualified success rate defined above, for at least 10 days following glaucoma surgery; or wherein the amount of nintedanib administered is effective to prolong bleb survival.

17. The method of claim 13, wherein nintedanib administration is performed before, during or after glaucoma surgery.

18. The method of claim 13, wherein nintedanib is in either a semi-solid or solid sustained-release implant is injected into the affected eye.

19. The method of claim 13, wherein the nintedanib is administered as a topical ocular formulation selected from a group consisting of a solution, suspension or emulsion.

20. The method of claim 13, wherein the glaucoma surgery is performed using classic trabeculectomy or a method selected from the group consisting of Trabectome, gonioscopy-assisted transluminal trabeculotomy, excimer laser trabeculostomy, and endoscopic cyclophotocoagulation.

21. The method of claim 13, wherein the glaucoma surgery performed is, for implanting an ocular filtration device.

22. The method of claim 21, wherein the ocular filtration device is an ocular stent.

23. The method of claim 13, wherein nintedanib is administered in combination with a cell-proliferation-inhibiting antimetabolite drug.

24. The method of claim 23, wherein the antimetabolite drug is selected from the group consisting of mitomycin C, 5-fluorouracil, floxuridine, cytarabine, 6-azauracil, azathioprine, methotrexate, mycophenolate mofetil, and thiotepa.

25. The method of claim 1, wherein the glaucoma surgery performed is a minimally invasive glaucoma surgery.

26. The method of claim 13, wherein the glaucoma surgery performed is a minimally invasive glaucoma surgery.

27. A method for improving success rate of implanting a stent in glaucoma surgery, comprising administering to an eye of a subject in need thereof a therapeutically effective amount of nintedanib or a pharmaceutically acceptable salt thereof.

* * * * *

UNITED STATES PATENT AND TRADEMARK OFFICE
CERTIFICATE OF CORRECTION

PATENT NO. : 10,335,408 B2  
APPLICATION NO. : 16/131945  
DATED : July 2, 2019  
INVENTOR(S) : Jinsong Ni and Rong Yang Page 1 of 1

It is certified that error appears in the above-identified patent and that said Letters Patent is hereby corrected as shown below:

On the Title Page

Column 2 in Other Publications, Line 25, delete "Placedo" and insert -- Placebo --, therefor.

Column 2 in Other Publications, Line 37, delete "homeostatis" and insert -- homeostasis --, therefor.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*